US008480427B2

(12) United States Patent
Marshalok

(10) Patent No.: US 8,480,427 B2
(45) Date of Patent: Jul. 9, 2013

(54) CABLE CONNECTOR

(75) Inventor: Brenda P. Marshalok, Savannah, GA (US)

(73) Assignee: BPM Medical, LLC, Savannah, GA (US)

( * ) Notice: Subject to any disclaimer, the term of this patent is extended or adjusted under 35 U.S.C. 154(b) by 91 days.

(21) Appl. No.: 13/187,174

(22) Filed: Jul. 20, 2011

(65) Prior Publication Data

US 2013/0023159 A1     Jan. 24, 2013

(51) Int. Cl.
*H01R 11/00* (2006.01)

(52) U.S. Cl.
USPC .......................................... 439/504; 607/37

(58) Field of Classification Search
USPC ................. 439/269.1, 504, 626, 628; 607/37
See application file for complete search history.

(56) References Cited

U.S. PATENT DOCUMENTS

| 5,679,022 | A  | * | 10/1997 | Cappa et al. ................... 439/502 |
| 6,113,415 | A  | * | 9/2000  | Bertsch et al. ................. 439/353 |
| 6,896,544 | B1 | * | 5/2005  | Kuelbs et al. .................. 439/504 |
| 7,633,023 | B1 | * | 12/2009 | Cappa et al. ............... 200/51.06 |
| 2005/0177199 | A1 | * | 8/2005 | Hansen et al. ................... 607/37 |

* cited by examiner

*Primary Examiner* — Renee Luebke
*Assistant Examiner* — Larisa Tsukerman
(74) *Attorney, Agent, or Firm* — Dunlap Codding, P.C.

(57) ABSTRACT

A cable connector for detachably connecting a lead having at least one contact to a system analyzer comprising a nonconductive base, a first conductive clip assembly connected to the base, and a second conductive clip assembly connected to the base. Each of the first and second conductive clip assemblies defining a lead contact receiving space which is in axial alignment with the other lead contact receiving space. The base further comprises a first base section and a second base section wherein the first conductive clip assembly is connected to the first base section and the second conductive clip assembly is connected to the second base section and wherein the first base section is selectively detachable from the second base section.

18 Claims, 4 Drawing Sheets

CABLE CONNECTOR

BACKGROUND OF THE INVENTION

1. Field of the Invention

The inventive concepts disclosed herein relate generally to cable connectors, and more particularly, but not by way of limitation, to a cable connector for testing installations of implantable stimulation leads implanted within a person's body.

2. Brief Description of Related Art

Advances in the medical field have made it possible for more people to have access to life-changing procedures. One of these procedures includes the installation of medical devices, such as pacemakers, within individuals to help regulate abnormal heart rhythms. These devices use electrical pulses to prompt the heart to beat at a normal rate. Medical devices such as these are normally attached by one of many various implantable stimulation electrical leads which are connected to a desired body tissue location.

These implanted leads include a conductor end in contact with the heart and a proximal end connected with the pulse generator. The proximal end typically includes one or more exposed contacts electrically connected with the distal conductor end. Proximal connectors used with most implantable stimulation leads are typically one of two types: unipolar or bipolar. Unipolar proximal connectors include a single proximal tip electrode (male connector) adapted to be inserted into an appropriate conductive annular ring or other receiving receptacle (female connector) located on or in the implantable stimulation device. Bipolar proximal connectors typically include a proximal tip electrode the same as is used in proximal unipolar connectors, and also include a proximal ring electrode, that is an annular conductive ring that is spaced-apart from the tip electrode.

Due to the seriousness and effect on the body from these types of surgeries, a need exists to verify that the installation of the implantable stimulation leads for the medical devices have been properly installed prior to the completion of a surgery to minimize the need for future, additional surgeries. The primary method currently utilized for testing the effectiveness of these installations is the use of medical device analyzers while the surgical procedure is in progress. During the surgery, the proximal end of the lead is connected to a system analyzer with a cable extending between the lead and the system analyzer. Although efforts have been made to standardize the size of proximal connectors, varying sizes and types of proximal connectors still exist, thus requiring the use of multiple cable connectors for each proximal connector which may be encountered.

To this end, a need exists for a cable connector that is adaptable for use in both unipolar and bipolar arrangements and with proximal connectors of varying sizes. It is to such a cable connector that the inventive concepts disclosed herein are directed.

DETAILED DESCRIPTION OF EXEMPLARY EMBODIMENTS

Figure 1:
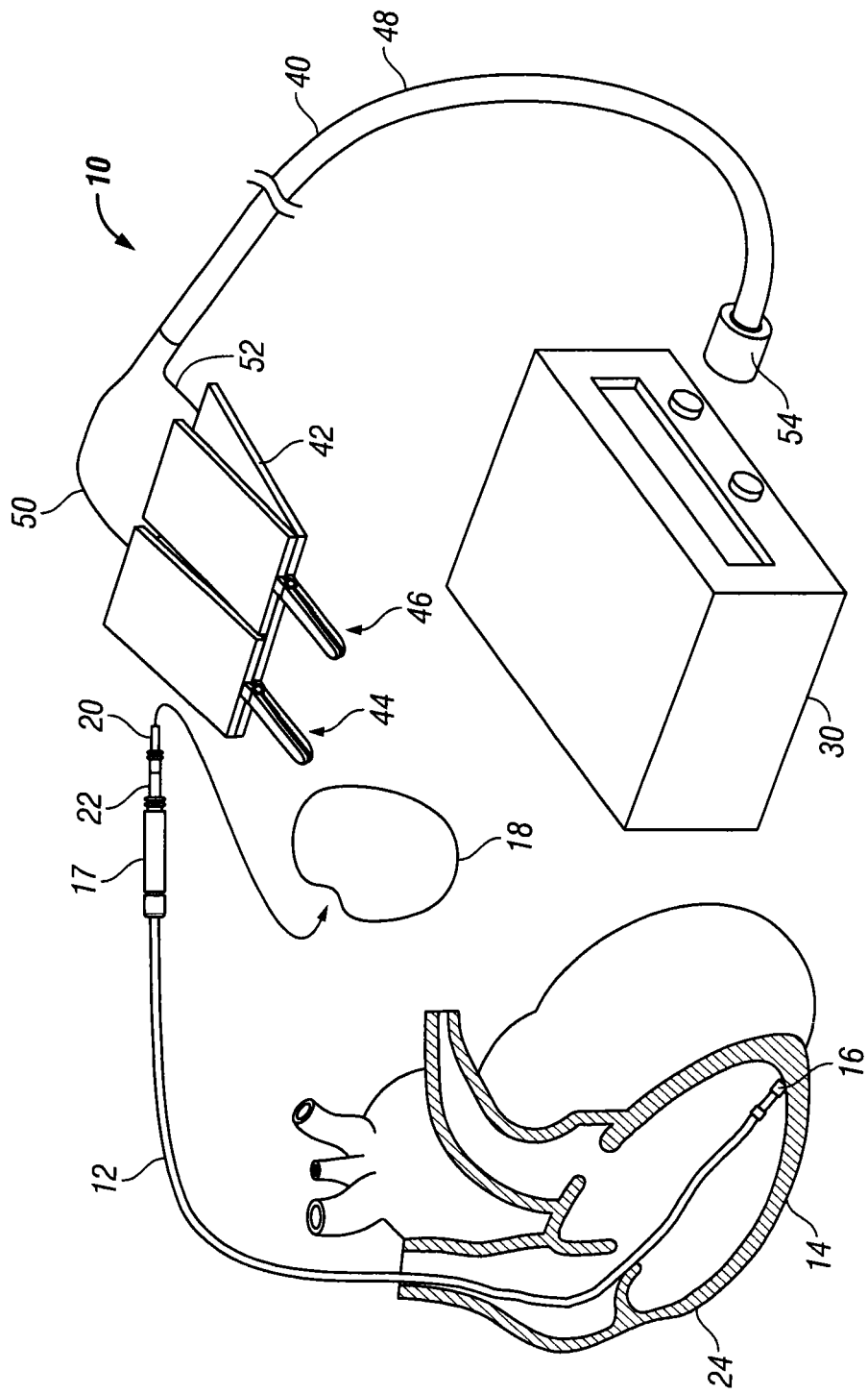
FIG. 1 is a diagrammatic perspective view illustrating a system embodying the inventive concepts disclosed herein for testing a lead intended to be connected to an electrical heart stimulator device.

Referring now to the drawings, and more particularly to FIG. 1, a system 10 for determining the efficacy of a connection of a lead 12 to a body tissue site 14 is illustrated. The lead 12 has a distal end 16 and a proximal end 17 and is intended for connecting an implantable electrical stimulation device 18 to the body tissue site 14. The proximal end 17 includes a plurality of proximate contacts, namely, a straight pin tip contact 20 and a ring contact 22. The system 10 incorporates features of the inventive concepts disclosed herein for use in association with the stimulation device 18, such as a pacemaker or cardioverter-defibrillator (ICD), providing electrical stimulation to a heart 24. Although the inventive concepts will be described with reference to the embodiments shown in the drawings, it should be understood that the inventive concepts can be embodied in many alternate forms or embodiments. In addition, any suitable size, shape or type of elements or materials could be used.

As described above, a physician verifies that the body tissue site selected for the implantation procedure is appropriate and will provide the desired result. For this reason, a system analyzer 30 is an integral component of the system 10. In short, the system analyzer 30 is an external testing and measuring device which, for example, can pace the heart during the implantation procedure and can measure stimulation thresholds, sensing thresholds, and lead impedance. The system analyzer 30 may also be used to test pulse generator function prior to implant, measure slew rate or print an electrogram of a sensed R-wave.

In order to use the system analyzer 30, it is necessary to connect the proximal end 17 of the lead 12 to the system analyzer 30. To achieve this result, a cable connector 40, constructed in accordance with the inventive concepts disclosed herein, is employed to releasably connect the proximal end 17 of the lead 12 to the system analyzer 30 so that the system analyzer 30 can be utilized to determine the efficacy of the chosen body tissue site 14.

Figure 2:
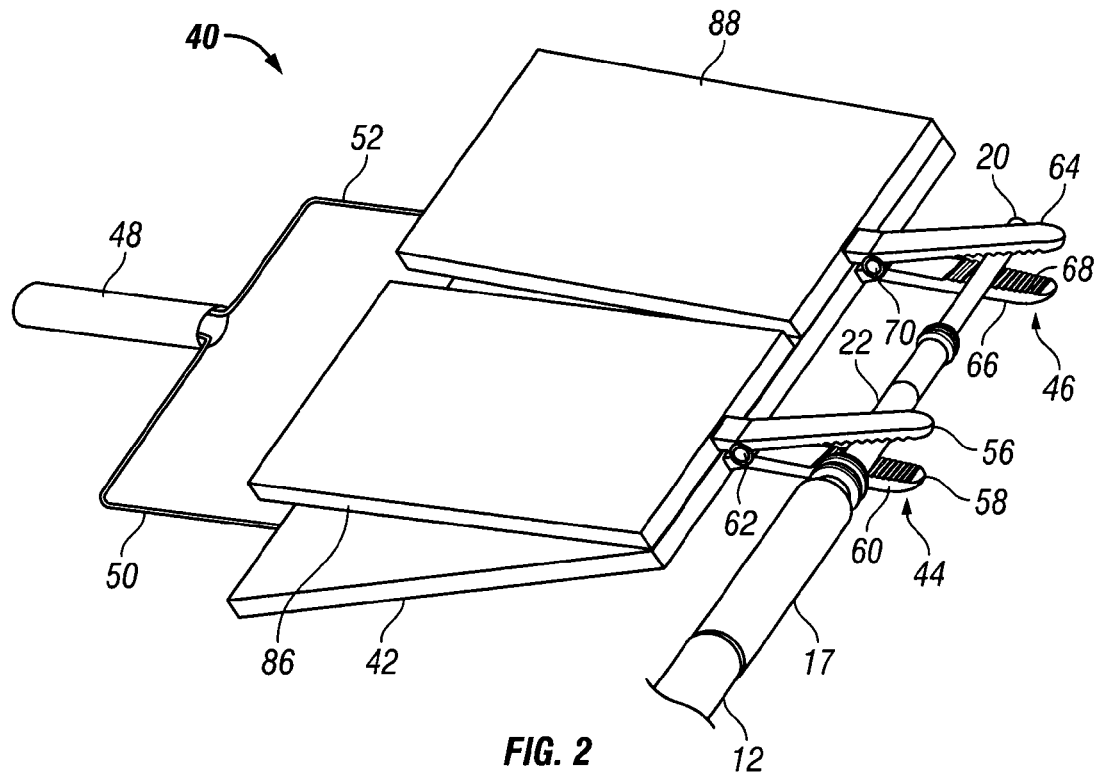
FIG. 2 is a perspective view of a cable connector constructed in accordance with the inventive concepts disclosed herein shown attached to a proximal end of a bipolar lead.
Figure 3:
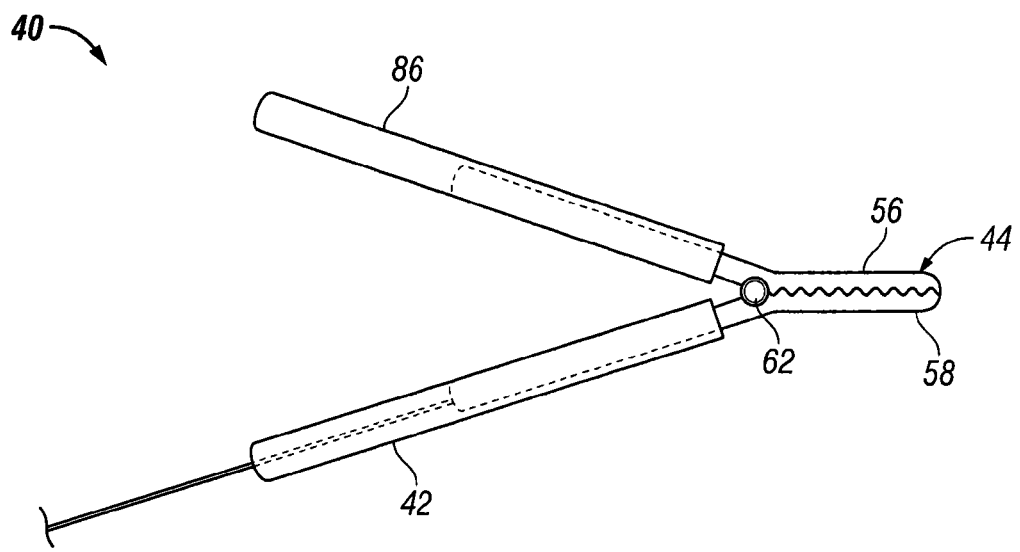
FIG. 3 is a side elevational view of the cable connector.

Referring now to FIGS. 2 and 3, the cable connector 40 includes a nonconductive base 42, a first clip assembly 44 connected to the base 42, a second clip assembly 46 connected to the base 42, and a system analyzer cable 48 electrically connected to the first and second clip assemblies 44 and 46 at one end and connectable to the system analyzer 30 at the other end. More particularly, the system analyzer cable 48 has one end containing two lead connections 50 and 52. The first lead connection 50 is electrically connected to the first clip assembly 44 and the second lead connection 52 is electrically connected to the second clip assembly 46. The opposite end of the system analyzer cable 48 is provided with a connector 54 for connecting to the system analyzer 30.

The first conductive clip assembly 44 includes a first clip member 56 and a second clip member 58 which cooperate with one another to define a first lead contact receiving space 60. The first clip member 56 and the second clip member 58 are pivotally connected with a first hinge mechanism 62 to permit relative movement of the first and second clip members 56 and 58 between a lead release position and a lead clip position (FIG. 2).

Similarly, the second conductive clip assembly 44 includes a third clip member 64 and a fourth clip member 66 which cooperate with one another to define a second lead contact receiving space 68. The third clip member 64 and the fourth clip member 66 are pivotally connected with a second hinge mechanism 70 to permit relative movement of the third and fourth clip members 64 and 66 between a lead release position and a lead clip position (FIG. 2). The second hinge mechanism 70 is independent from the first hinge mechanism 62 such that the position of the first clip member 56 relative to the position of the second clip member 58 may be different than the position of the third clip member 64 relative to the fourth clip member 66.

As best shown in FIG. 2, the first and second conductive clip assemblies 44 and 46 are connected to the base 42 such that the first contact lead receiving space 60 defined by the first and second clip members 56 and 58 is in axial alignment with the second lead contact receiving space 68 defined by the third and fourth clip members 64 and 66. The axial alignment of the first and second lead contact receiving spaces 60 and 68, along with the independence of the first and second hinge mechanisms 62 and 70 permit the first clip assembly 44 to be operably attached to one portion of the proximal end 17 of the lead 12 and the second clip assembly 46 to be operably attached to another portion of the proximal end 17 of the lead 12 even though the two portions of the lead 12 may have diameters of different sizes. By way of example, the first clip assembly 44 is shown to be operably attached to the ring contact 22 of the lead 12 and the second clip assembly 46 is shown to be operably attached to the pin contact 20.

In one embodiment, the first and second clip assemblies 44 and 46 may each be in the form of a device commonly know as an "alligator clip" wherein the first and second clip assemblies 44 and 46 each have two tapered, serrated jaws pinned to one another so that the jaws can pivot relative to one another between an open position and a closed position. The jaws are biased in the closed position by a spring.

Referring to FIG. 3, the nonconductive base 42 is illustrated to be a generally planar member with the first and second clip assemblies 44 and 46 embedded in or otherwise connected to the base 42. The base 42 may be formed of any non-conductive material, such as a polyvinyl. As illustrated, the second and fourth clip members 58 and 66 may be molded into the base 42, or the second and fourth clip members 58 and 66 may be connected to the base 42 in some other suitable fashion.

In one embodiment, the base 42 comprises a first base section 72 and a second base section 74 that are selectively detachable from one another. To this end, the first conductive clip assembly 44 is connected to the first base section 72 and the second conductive clip assembly 46 is connected to the second base section 74 such that first clip assembly 44 and the second clip assembly 46 may be moved relative to one another when detached from one another. More particularly, when the cable connector 40 is employed with a lead having a unipolar proximal end, the first clip assembly 44 may be attached to the proximal end of the lead 12 while the second clip assembly 46 may be attached to the patient's tissue in order to complete the electrical circuit.

Figure 4A:
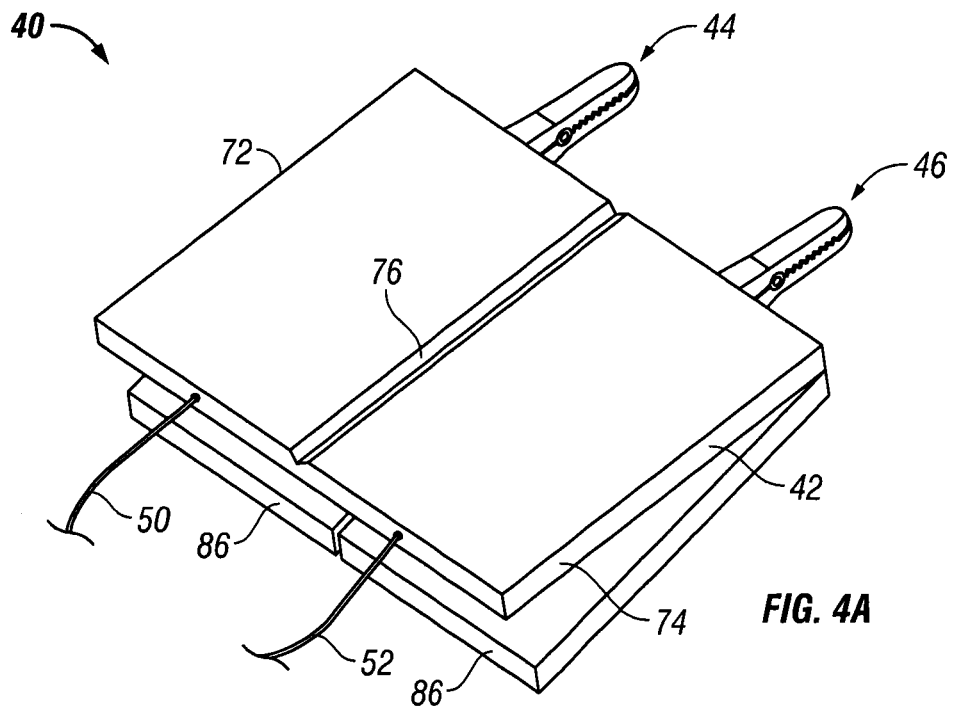
FIG. 4A is a bottom perspective view of the cable connector of FIG. 2 showing a base in an attached condition.
Figure 4B:
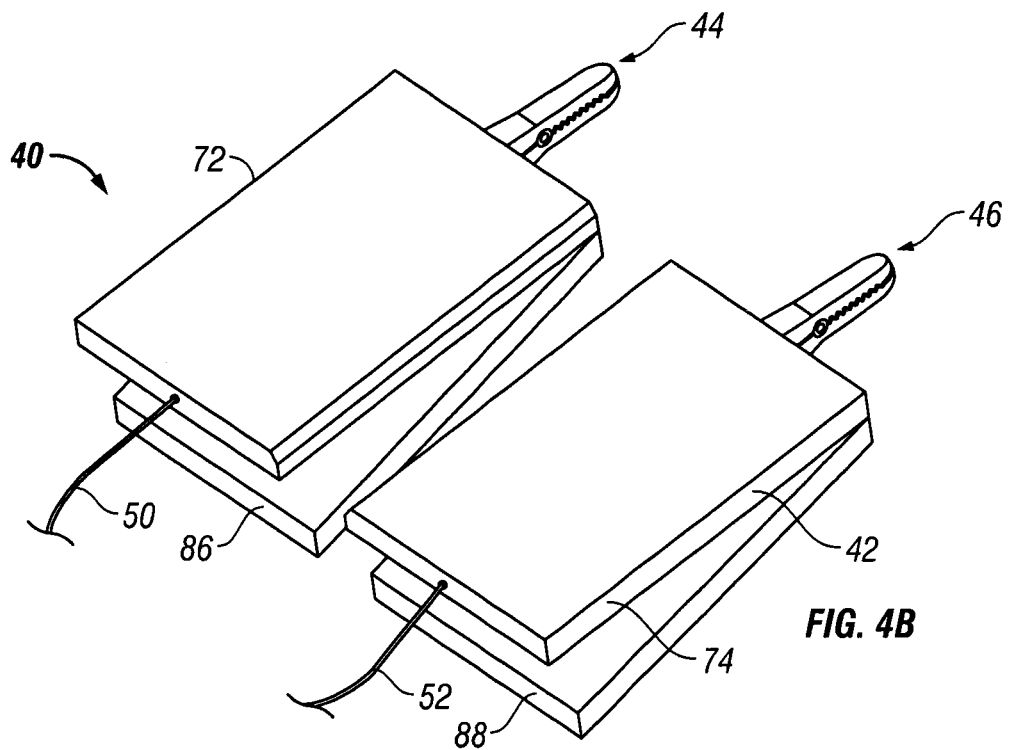
FIG. 4B is a bottom perspective view of the cable connector of FIG. 2 showing the base in a detached condition.

Referring now to FIGS. 4A and 4B, to effect detachment of the first base section 72 from the second base section 74, the base 42 may be provided with a transverse score line 76 delineating the first base section 72 from the second base section 74. The transverse score line 76 is formed to facilitate selective detachment, as shown in FIG. 4B, of the first base section 72 from the second base section 74. It will be appreciated that the score line 76 may be constructed in a variety of forms. For example, the score line 76 may be in the form of perforations. It should further be appreciated that with the score line embodiment, the first and second base sections 72 and 74 are not intended to be reattached to one another after separation has occurred.

Figure 5A:
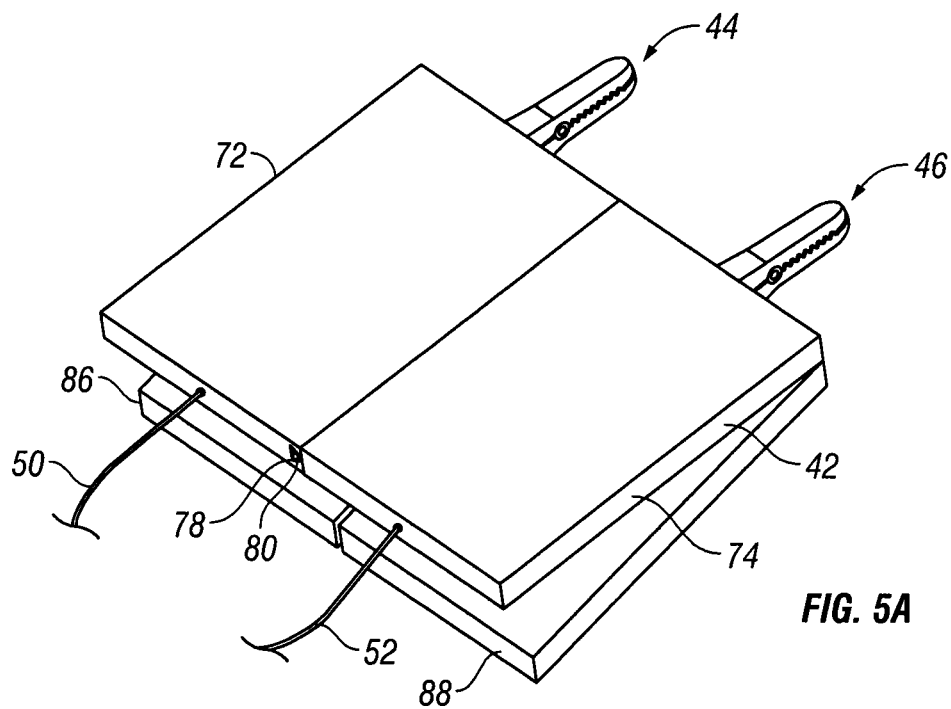
FIG. 5A is a bottom perspective view of another embodiment of a cable connector showing a base in an attached condition.
Figure 5B:
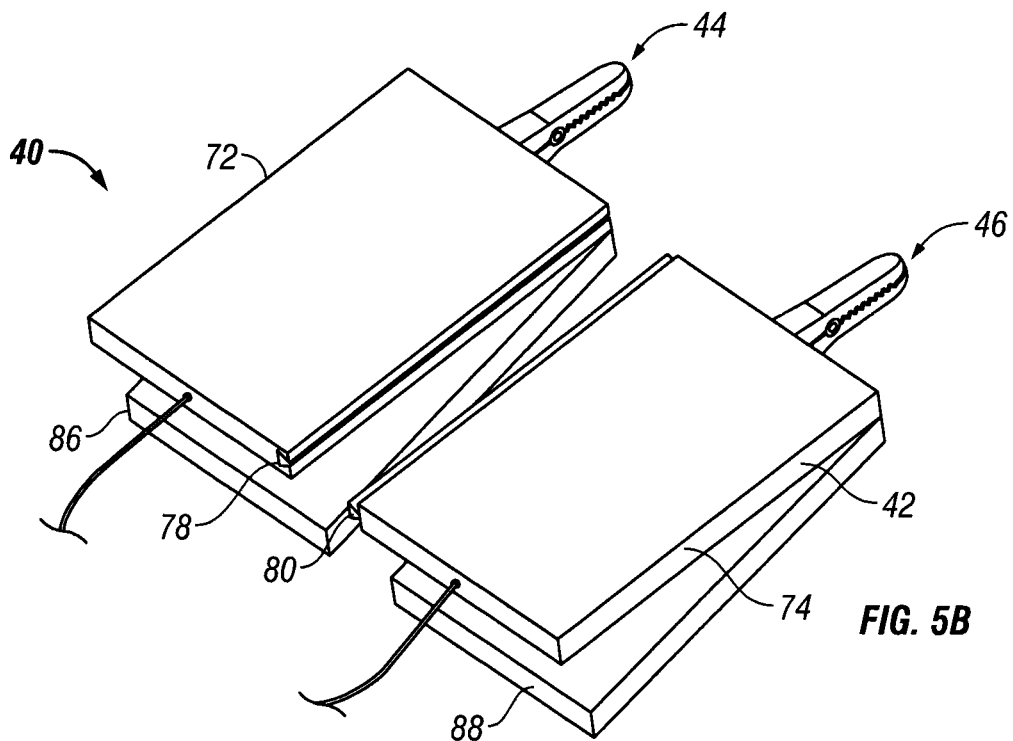
FIG. 5B is a bottom perspective view of the cable connector of FIG. 5A showing the base in a detached condition.

In another embodiment illustrated in FIGS. 5A and 5B, the first base section 72 may be provided with a first connector member 78 and the second base section 74 provided with a second connector member 80 such that the second connector member 80 of the second base section 74 is selectively engageable and disengageable from the first connector member 78 of the first base section 72. By way of example, the first connector member 78 may be a groove formed in an edge of the first base section 72 and the second connector member 80 may be a tongue projecting away from an edge of the second base section 74 in such a way as to slidably received by the groove of the first base section 72. It should be appreciated, however, that other suitable connecting members may be employed, such as a post and channel fitting (male-female), ball and socket (snap-together), screw twist fitting, pressure fitting with a flange snap-in connection, or any removable coupler that would clamp or clip the base sections together.

To facilitate actuation of the first and second clip assemblies 44 and 46 from the lead clip position to the lead release position, the cable connector 40 may be provided with finger tabs 86 and 88 to which the first and third clip members 56 and 64, respectively, are connected. The finger tabs 86 and 88 may be formed of the same material and of a similar shape as the base 42 with the exception that the finger tabs 86 and 88 are spaced apart from one another to permit movement of one of the finger tabs 86 and 88 relative to the other finger tab. To facilitate simultaneous actuation of the first clip assembly 44 and the second clip assembly 46 with one hand of an individual, the finger tabs 86 and 88 may be spaced apart from one another a distance that permits a thumb or finger of an individual to be positioned on each of the tabs 86 and 88 simultaneously to permit simultaneous movement of the first and second clip assemblies by force applied simultaneously to the first and second finger tabs 86 and 88 and transmitted to the first and third clip members 56 and 64 by the finger or thumb of the individual.

The cable connector assembly 40 described above allows for the use of one cable connector to be used for both unipolar and bipolar testing configurations. Additionally, the unity, and yet independence, of the first clip assembly 44 and the second clip assembly 46 provide the advantage of quick attachment to a proximal connector and the flexibility to receive varying sizes of proximal connectors.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims

What is claimed is:
1. A cable connector, comprising:
 a nonconductive base having a first base section and a second base section, the first base section being selectively detachable from the second base section;

a first conductive clip assembly connected to the first base section and including a first clip member and a second clip member, the first clip member and the second clip member of the first conductive clip assembly cooperating to define a first lead contact receiving space;

a first hinge mechanism pivotally connecting the first clip member and the second clip member of the first conductive clip assembly for relative movement between a lead release position and a lead clip position;

a second conductive clip assembly connected to the second base section and including a third clip member and a fourth clip member, the third clip member and the fourth clip member of the second conductive clip assembly cooperating to define a second lead contact receiving space which is in axial alignment with the first lead contact receiving space of the first conductive clip assembly; and a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member.

2. The cable connector of claim 1 wherein the base is a substantially planar member having a transverse score line separating the first base section from the second base section, the transverse score facilitating selective detachment of the first base section from the second base section.

3. The cable connector of claim 1 wherein the base is a substantially planar member, and wherein the first base section has a first connector member and the second base section has a second connector member, the second connector member of the second base section being selectively engageable and disengageable from the first connector member of the first base section.

4. The cable connector of claim 3 wherein the first connector member is a tongue extending from an edge of the first base section and the second connector member is a groove projecting inwardly from an edge of the second base section in such a way as to slidably receive the tongue of the first base section.

5. A cable connector, comprising:

a nonconductive base;

a first conductive clip assembly connected to the base and including a first clip member and a second clip member, the first clip member and the second clip member of the first conductive clip assembly cooperating to define a first lead contact receiving space;

a first hinge mechanism pivotally connecting the first clip member and the second clip member of the first conductive clip assembly for relative movement between a lead release position and a lead clip position;

a second conductive clip assembly connected to the base and including a third clip member and a fourth clip member, the third clip member and the fourth clip member of the second conductive clip assembly cooperating to define a second lead contact receiving space which is in axial alignment with the first lead contact receiving space of the first conductive clip assembly;

a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member; and a first finger tab connected to the first clip member and a second finger tab connected to the third clip member, the first and second finger tabs spaced apart from one other to permit movement of the first and second finger tabs relative to one another and permit simultaneous movement of the first and second clip assemblies by force applied simultaneously to the first and second finger tabs by a finger or thumb of an individual and transmitted to the first and third clip members.

6. A cable connector, comprising:

a nonconductive base including a first base section and a second base section, the first base section being selectively detachable from the second base section;

a first conductive clip assembly connected to the first base section of the base and including a first clip member and a second clip member, the first clip member and the second clip member of the first conductive clip assembly cooperating to define a first lead contact receiving space;

a first hinge mechanism pivotally connected the first clip member and the second clip member of the first conductive clip assembly for relative movement between a lead release position and a lead clip position;

a second conductive clip assembly connected to the second base section of the base and including a third clip member and a fourth clip member, the third clip member and the fourth clip member of the second conductive clip assembly cooperating to define a second lead contact receiving space;

a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member; and a first finger tab connected to the first clip member and a second finger tab connected to the third clip member, the first and second finger tabs spaced apart from one other to permit movement of the first and second finger tabs relative to one another and permit simultaneous movement of the first and second clip assemblies by force applied simultaneously to the first and second finger tabs by a finger or thumb of an individual and transmitted to the first and third clip members.

7. The cable connector of claim 6 wherein the base is a substantially planar member having a transverse score line separating the first base section from the second base section, the transverse score facilitating selective detachment of the first base section from the second base section.

8. The cable connector of claim 6 wherein the base is a substantially planar member, and wherein the first base section has a first connector member and the second base section has a second connector member, the second connector member of the second base section being selectively engageable and disengageable from the first connector member of the first base section.

9. The cable connector of claim 8 wherein the first connector member is a tongue extending from an edge of the first base section and the second connector member is a groove projecting inwardly from an edge of the second base section in such a way as to slidably receive the tongue of the first base section.

10. A cable connector for detachably connecting a lead having at least one contact to a system analyzer, the cable connector comprising:
   a nonconductive base having a first base section and a second base section, the first base section being selectively detachable from the second base section;
   a first conductive clip assembly connected to the first base section and including a first clip member and a second clip member, the first clip member and the second clip member of the first conductive clip assembly cooperating to define a first lead contact receiving space;
   a first hinge mechanism pivotally connecting the first clip member and the second clip member of the first conductive clip assembly for relative movement between a lead release position and a lead clip position;
   a second conductive clip assembly connected to the second base section and including a third clip member and a fourth clip member, the third clip member and the fourth clip member of the second conductive clip assembly cooperating to define a second lead contact receiving space which is in axial alignment with the first lead contact receiving space of the first conductive clip assembly;
   a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member; and
   a system analyzer cable electrically connected to the first and second conductive clip assemblies and electrically connectable to the system analyzer.

11. The cable connector of claim 10 wherein the base is a substantially planar member having a transverse score line separating the first base section from the second base section, the transverse score facilitating selective detachment of the first base section from the second base section.

12. The cable connector of claim 10 wherein the base is a substantially planar member, and wherein the first base section has a first connector member and the second base section has a second connector member, the second connector member of the second base section being selectively engageable and disengageable from the first connector member of the first base section.

13. The cable connector of claim 12 wherein the first connector member is a tongue extending from an edge of the first base section and the second connector member is a groove projecting inwardly from an edge of the second base section in such a way as to slidably receive the tongue of the first base section.

14. A cable connector for detachably connecting a lead having at least one contact to a system analyzer, the cable connector comprising:
   a nonconductive base;
   a first conductive clip assembly connected to the base and including a first clip member and a second clip member, the first clip member and the second clip member of the first conductive clip assembly cooperating to define a first lead contact receiving space;
   a first hinge mechanism pivotally connecting the first clip member and the second clip member of the first conductive clip assembly for relative movement between a lead release position and a lead clip position;
   a second conductive clip assembly connected to the base and including a third clip member and a fourth clip member, the third clip member and the fourth clip member of the second conductive clip assembly cooperating to define a second lead contact receiving space which is in axial alignment with the first lead contact receiving space of the first conductive clip assembly;
   a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member;
   a first finger tab connected to the first clip member and a second finger tab connected to the third clip member, the first and second finger tabs spaced apart from one other to permit movement of the first and second finger tabs relative to one another and permit simultaneous movement of the first and second clip assemblies by force applied simultaneously to the first and second finger tabs by a finger or thumb of an individual and transmitted to the first and third clip members; and
   a system analyzer cable electrically connected to the first and second conductive clip assemblies and electrically connectable to the system analyzer.

15. A cable connector for detachably connecting a lead having at least one contact to a system analyzer, the cable connector comprising:
   a nonconductive base including a first base section and a second base section, the first base section being selectively detachable from the second base section;
   a first conductive clip assembly connected to the first base section of the base and including a first clip member and a second clip member, the first clip member and the second clip member of the first conductive clip assembly cooperating to define a first lead contact receiving space;
   a first hinge mechanism pivotally connected the first clip member and the second clip member of the first conductive clip assembly for relative movement between a lead release position and a lead clip position;
   a second conductive clip assembly connected to the second base section of the base and including a third clip member and a fourth clip member, the third clip member and the fourth clip member of the second conductive clip assembly cooperating to define a second lead contact receiving space;
   a second hinge mechanism pivotally connecting the third clip member and the fourth clip member of the second conductive clip assembly for relative movement between a lead release position and a lead clip position, the second hinge mechanism being independent from the first hinge mechanism such that the position of the first clip member relative to the position of the second clip member may be different than the position of the third clip member relative to the fourth clip member;
   a system analyzer cable electrically connected to the first and second conductive clip assemblies and electrically connectable to the system analyzer; and
   a first finger tab connected to the first clip member and a second finger tab connected to the third clip member, the first and second finger tabs spaced apart from one other to permit movement of the first and second finger tabs relative to one another and permit simultaneous movement of the first and second clip assemblies by force applied simultaneously to the first and second finger tabs by a finger or thumb of an individual and transmitted to the first and third clip members.

16. The cable connector of claim 15 wherein base is a substantially planar member having a transverse score line separating the first base section from the second base section, the transverse score facilitating selective detachment of the first base section from the second base section.

17. The cable connector of claim 15 wherein base is a substantially planar member, and wherein the first base section has a first connector member and the second base section has a second connector member, the second connector member of the second base section being selectively engageable and disengageable from the first connector member of the first base section.

18. The cable connector of claim 17 wherein the first connector member is a tongue extending from an edge of the first base section and the second connector member is a groove projecting inwardly from an edge of the second base section in such a way as to slidably receive the tongue of the first base section.

* * * * *